US010842657B2

(12) United States Patent
Lonn et al.

(10) Patent No.: US 10,842,657 B2
(45) Date of Patent: Nov. 24, 2020

(54) BRAIDED STENT CROWN GEOMETRY AND FLARE

(71) Applicant: Cook Medical Technologies LLC, Bloomington, IN (US)

(72) Inventors: Melissa Lonn, Lafayette, IN (US); Shuo Yang, W. Lafayette, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 126 days.

(21) Appl. No.: 16/052,308

(22) Filed: Aug. 1, 2018

(65) Prior Publication Data
US 2019/0053925 A1 Feb. 21, 2019

Related U.S. Application Data

(60) Provisional application No. 62/547,916, filed on Aug. 21, 2017.

(51) Int. Cl.
A61F 2/06 (2013.01)
A61F 2/90 (2013.01)
A61F 2/86 (2013.01)
A61F 2/88 (2006.01)

(52) U.S. Cl.
CPC .......... A61F 2/90 (2013.01); A61F 2/06 (2013.01); A61F 2/86 (2013.01); A61F 2/88 (2013.01); A61F 2220/0008 (2013.01); A61F 2230/005 (2013.01); A61F 2250/0039 (2013.01)

(58) Field of Classification Search
CPC ...... A61F 2/82; A61F 2/06; A61F 2/92; A61F 2/90; A61F 2/88

USPC ................................. 623/1.15–1.48
See application file for complete search history.

(56) References Cited

U.S. PATENT DOCUMENTS

| 6,565,597 | B1 | 5/2003 | Fearnot et al. |
| 8,623,071 | B2* | 1/2014 | Lundkvist ............ A61F 2/90 623/1.15 |
| 8,778,011 | B2* | 7/2014 | Ryan ................... A61F 2/90 623/1.15 |
| 8,978,533 | B2 | 3/2015 | Cattaneo et al. |
| 9,173,733 | B1 | 11/2015 | Lim et al. |

(Continued)

FOREIGN PATENT DOCUMENTS

| DE | 202015105466 U1 | 11/2015 |
| WO | WO 0049971 | 8/2000 |

(Continued)

OTHER PUBLICATIONS

Krischeck, ö., "A Comparison of Functional and Physical Properties of Self-Expanding Intracranial Stents [Neuroform3, Wingspan, Solitaire, Leo (+), Enterprise]," Minim Invas Neurosurg, 2011; 54; 21-28.

(Continued)

Primary Examiner — Suzette J Gherbi
(74) Attorney, Agent, or Firm — Brinks Gilson & Lione

(57) ABSTRACT

Disclosed herein is a stent which is compressible to small diameter and usable in neurovascular applications. The device is a braided stent and has a crown geometry which enables compression to small diameter without cracking or tangling. Also disclosed is a method of deploying a stent to a body vessel and its use in a coiling procedure.

20 Claims, 7 Drawing Sheets

(56) References Cited

U.S. PATENT DOCUMENTS

| | | | |
|---|---|---|---|
| 9,320,623 B2 | 4/2016 | Ryan et al. | |
| 9,439,791 B2 | 9/2016 | Vong et al. | |
| 2009/0054972 A1* | 2/2009 | Norton | D04C 1/06 |
| | | | 623/1.53 |
| 2011/0079315 A1* | 4/2011 | Norton | A61F 2/90 |
| | | | 140/71 R |
| 2012/0259407 A1 | 11/2012 | Clerc et al. | |
| 2012/0310319 A1 | 12/2012 | Tieu et al. | |
| 2013/0231734 A1* | 9/2013 | Clerc | A61F 2/885 |
| | | | 623/1.22 |
| 2014/0277371 A1 | 9/2014 | Ryan | |
| 2014/0277560 A1 | 9/2014 | Walak | |
| 2014/0288637 A1* | 9/2014 | Clerc | A61F 2/82 |
| | | | 623/1.22 |
| 2015/0081000 A1 | 3/2015 | Hossainy et al. | |
| 2015/0134074 A1 | 5/2015 | Walsh et al. | |
| 2015/0173919 A1 | 6/2015 | Baldwin | |
| 2015/0174099 A1 | 6/2015 | Barrett et al. | |
| 2015/0282960 A1 | 10/2015 | Harris | |
| 2016/0199204 A1 | 7/2016 | Pung et al. | |
| 2017/0105854 A1* | 4/2017 | Treacy | A61F 2/90 |
| 2018/0271682 A1* | 9/2018 | Treacy | A61F 2/88 |
| 2019/0262151 A1* | 8/2019 | Treacy | A61F 2/90 |

FOREIGN PATENT DOCUMENTS

| | | |
|---|---|---|
| WO | WO 2013/052528 A1 | 4/2013 |
| WO | WO 2015135658 | 9/2015 |

OTHER PUBLICATIONS

Extended European Search Report in European Application No. 18185312.8-1113 dated Jan. 17, 2019 (6 pages).

* cited by examiner

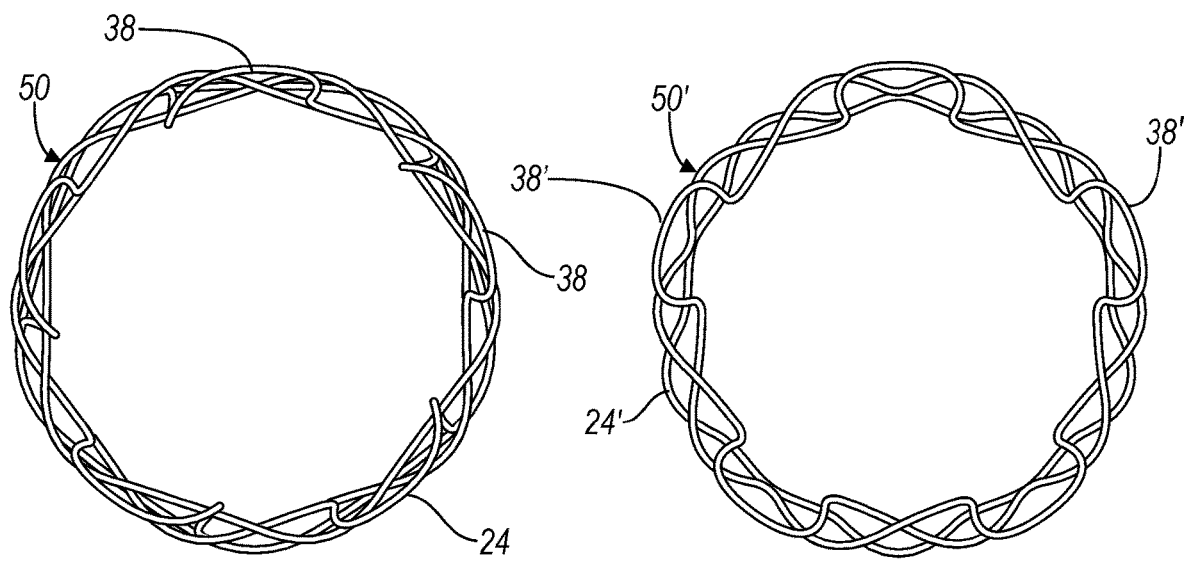
FIG. 4A
FIG. 4B
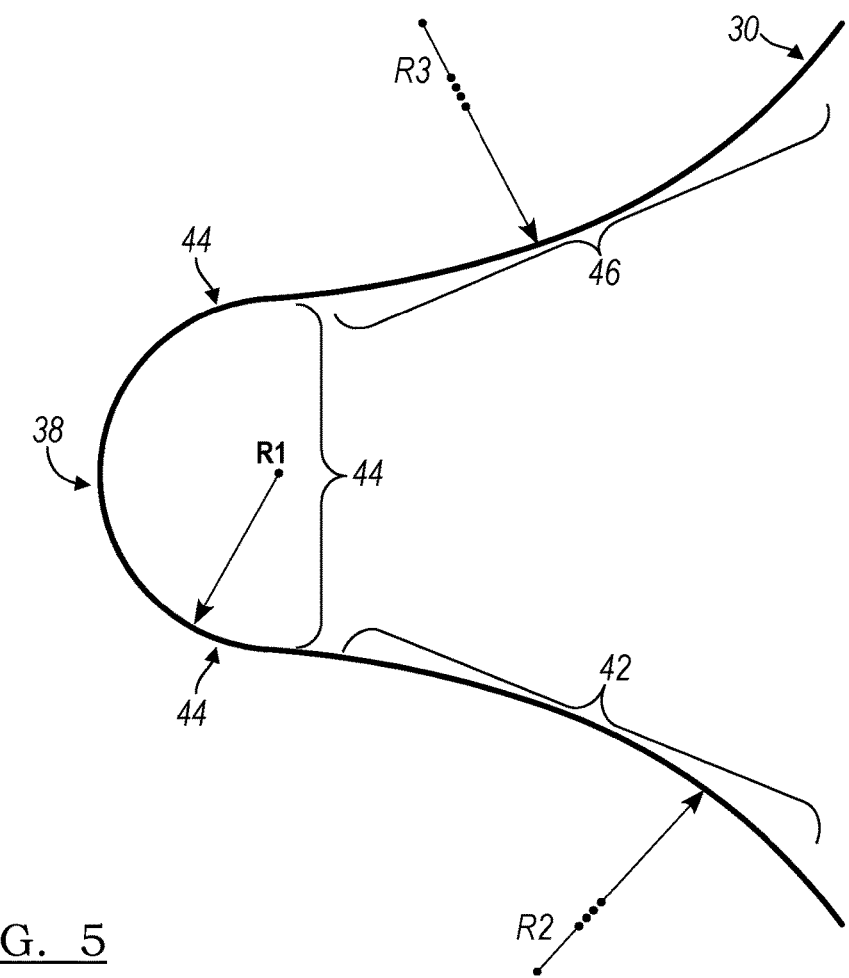
FIG. 5

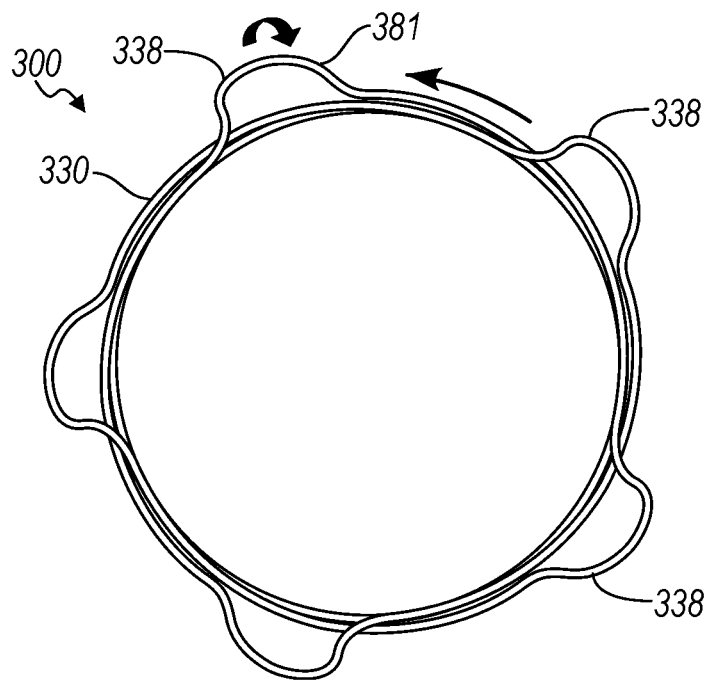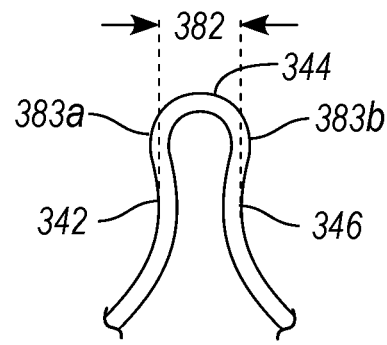
FIG. 8A
FIG. 8B
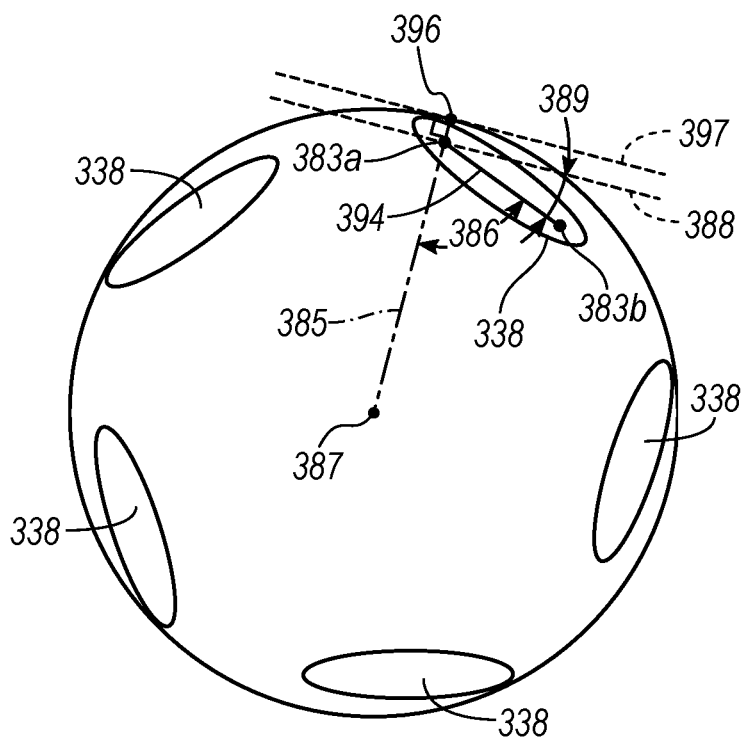
FIG. 8C

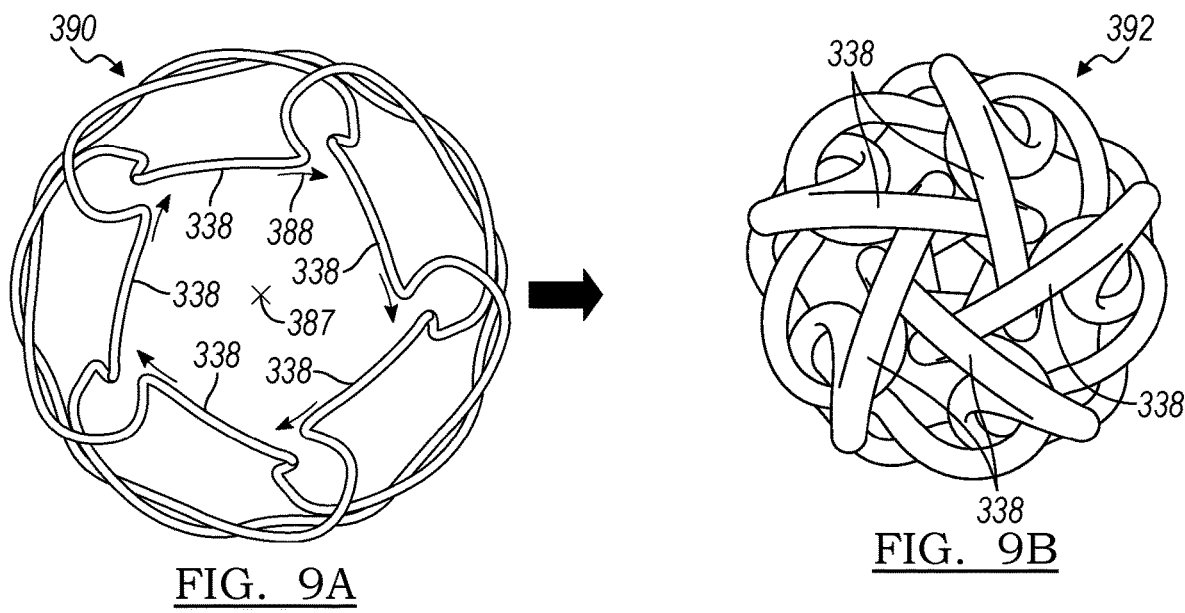
FIG. 9A
FIG. 9B
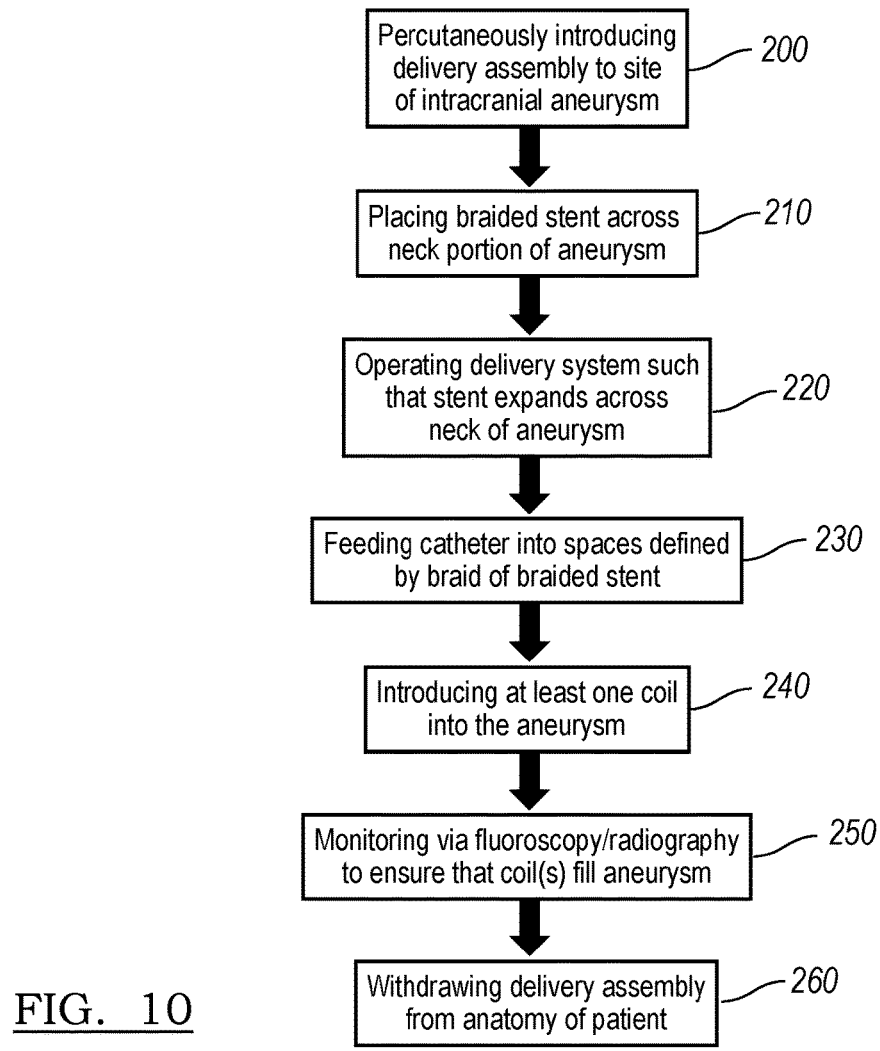
FIG. 10

BRAIDED STENT CROWN GEOMETRY AND FLARE

BACKGROUND

The present application generally relates to medical devices. More particularly, the present application relates to braided stents for use in delivery to a body vessel in need of treatment, in some cases a neurovascular body lumen.

Stents and other implantable medical devices which incorporate stents are in widespread use in the medical field for dilating patient's vessels, for closing off aneurysms, for treating vascular dissections, for supporting prosthetic elements and so on. Stents have the function of holding the vessel open or for holding a device securely against the vessel wall to effect a good seal as well as to prevent device migration (such as bridging the neck of an aneurysm which has been filled with occlusion coils in order to ensure that the coils do not migrate into the main vessel.) As a result, it is desirable for the stent to be able to apply an opening force and to do so reliably. Self-expanding implants, in particular, are selected for such applications due to the assurance that they will expand to fit the vessels in which they are implanted, allow for less-complicated delivery schemes, and have a tendency to remain in the specific location to which they have been delivered.

Embolic coiling is a standard treatment for intracranial systems. However, aneurysms with complicated geometries (such as wide-necked aneurysms, fusiform aneurysms, bi-lobed aneurysms, and the like) may be difficult to treat with embolic coils alone. In some cases, the coils will not be fully trapped within the aneurysm, causing embolic problems in the parent artery. Stent-assisted coiling has arisen as a solution to this problem. A stent is placed across the neck of the aneurysm in the parent vessel. Coils are then placed within the aneurysm. The stent structure prevents coils from protruding into the parent artery.

Braided stents are well-suited for such a coiling application owing to their flexibility, their ability to conform to the neurovasculature, and the fact that they can be built with small pores to prevent coils from protruding into the parent vessel. However, braided wires forming crowns, end-rings, or similar structures at either end of the stent may in some cases be susceptible to fracture and entanglement, particularly when compressed to a small diameter for delivery in a delivery assembly.

It has been a challenge to develop a braided stent that will allow for crimping to a small diameter without fracturing or tangling.

SUMMARY

In one aspect, the present disclosure provides a stent constructed from a wire braided into a tubular body. The stent includes a proximal end and extends to a distal end. The tubular body has an expanded configuration and a collapsed configuration and terminates in a crown in at least one of the proximal end and the distal end. The crown defines a plurality of rounded tips, each rounded tip including a first bend, a second bend, and a third bend. The second bend is positioned between and is connected to the first bend and the third bend. The first bend and the third bend are concave and have a first radius of curvature, the second bend being convex and having a second radius of curvature between about one-half to about one-quarter the first radius of curvature.

In another aspect, the present disclosure provides a stent for treatment of an intracranial aneurysm. The stent includes a wire braided into a tubular body comprising a proximal end and extending to a distal end. The tubular body has an expanded configuration and a collapsed configuration. The stent includes a central portion having a first diameter in the expanded configuration and a proximal portion extending proximally from the central portion to a proximal end and including a proximal crown. The proximal portion is flared such that the proximal end has a larger diameter than the first diameter in the expanded configuration. The stent also includes a distal portion extending distally from the central portion to a distal end and includes a distal crown. The distal portion is flared such that the distal end has a larger diameter than the first diameter in the expanded configuration. Each of the proximal crown and the distal crown define a plurality of rounded tips. Each rounded tip includes a first bend, a second bend, and a third bend. The second bend is positioned between and is connected to the first bend and the third bend. The first bend and the third bend are concave and have a first radius of curvature. The second bend is convex and has a second radius of curvature between about one-half to about one-quarter the first radius of curvature.

In another aspect, the present disclosure provides a method of treating an intracranial aneurysm. The method includes a first step of percutaneously introducing a delivery assembly to a site of treatment including the intracranial aneurysm within the vasculature of a patient. The method further includes implanting a stent across a neck portion of the intracranial aneurysm, the stent including a wire braided into a tubular body, the tubular body having an expanded configuration and a collapsed configuration. The tubular body includes a proximal end and extends to a distal end. The tubular body defines a lumen therethrough, the tubular body terminating in a crown in at least one of the proximal end and the distal end, the crown defining a plurality of rounded tips, each rounded tip including a first bend, a second bend, and a third bend. The second bend is positioned between and connected to the first bend and the third bend. The first bend and the third bend have a first radius of curvature, and the second bend has a second radius of curvature between about one-half to about one-quarter the first radius of curvature. The stent includes a plurality of pores between intersecting portions of the braided wire. In another step, the method includes operating the delivery system to allow the stent to expand from the collapsed configuration to the expanded configuration. In another step, the method includes disposing an open end of a delivery catheter through one of the plurality of pores and into the aneurysm. In a further step, the method includes introducing at least one coil or a quantity of embolic material through the open end of the delivery catheter and into the aneurysm.

Further objects, features and advantages of this system will become readily apparent to persons skilled in the art after a review of the following description, with reference to the drawings and claims that are appended to and form a part of this specification.

BRIEF DESCRIPTION OF THE DRAWINGS

FIG. 4A is an end view of a braided stent constructed in accordance with the principles of the present disclosure, showing wall apposition when implanted into a vessel of a first diameter;

FIG. 4B is an end view of the braided stent of FIG. 4A showing wall apposition when implanted into a vessel of a second diameter;

FIG. 5 is a diagram of an end bend structure for a braided stent constructed in accordance with the principles of the present disclosure;

FIG. 8A is an end view of a braided stent in an unconstrained configuration constructed in accordance with the principles of an embodiment of the present disclosure;

FIG. 8B is a side view of an portion of the device of FIG. 8A including a single tip;

FIG. 8C is a schematic end view of the device of FIG. 8A showing various features thereof;

FIG. 9A is an end view of the device of FIG. 8A in a partially collapsed configuration;

FIG. 9B is an end view of the device of FIG. 8A in a fully collapsed configuration; and FIG. 10 is a flowchart describing steps of a method of using a braided stent in accordance with the embodiments of the present disclosure.

DETAILED DESCRIPTION

The drawings are purely schematic illustrations of various aspects of the invention and are not necessarily to scale, unless expressly stated.

The terms "substantially" or "about" used herein with reference to a quantity includes variations in the recited quantity that are equivalent to the quantity recited, such as an amount that is equivalent to the quantity recited for an intended purpose or function. "Substantially" or derivatives thereof will be understood to mean significantly or in large part. When used in the context of a numerical value or range set forth, "about" or "substantially" means a variation of ±15%, or less, of the numerical value. For example, a value differing by ±15%, ±14%, ±10%, or ±5%, among others, would satisfy the definition of "about."

Figure 1:
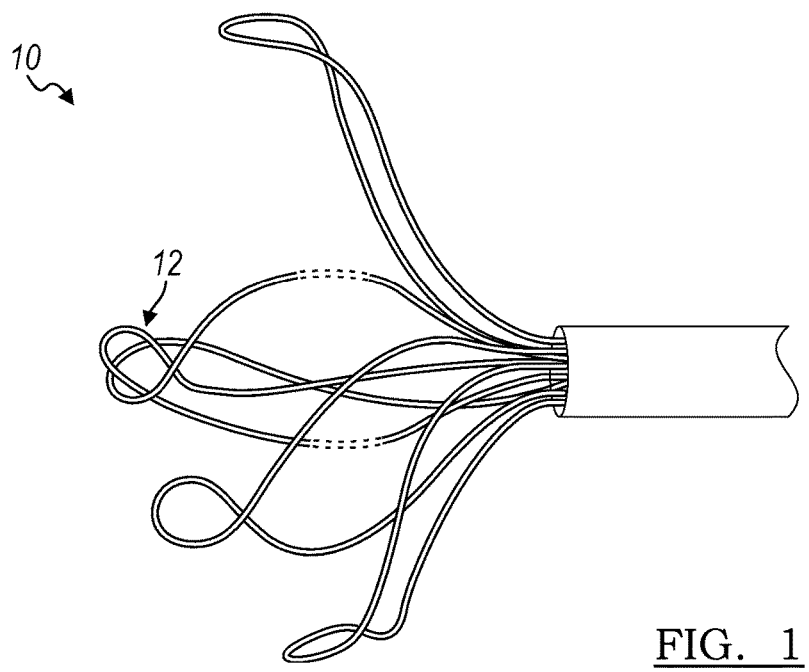
FIG. 1 is a side view of an end of a prior art stent.

Due to their flexibility and ability to realize excellent wall apposition, braided stents are particularly well suited for procedures involving the vasculature of the brain, neck, and spinal cord, specifically those small vessels which are susceptible to developing aneurysms. The secure fit of a braided stent can aid in retaining coils that are placed within the aneurysm. However, the small size of these vessels may require a delivery system which is of low profile. The structure of braided stents, particularly those constructed of a single wire, can lead these devices to fracture, tangle, or both during compression into the delivery system. FIG. 1 illustrates the end of a prior art braided stent 10 in which the apices of the device 12 have become entangled with nearby apices at the device end.

Figure 2A:
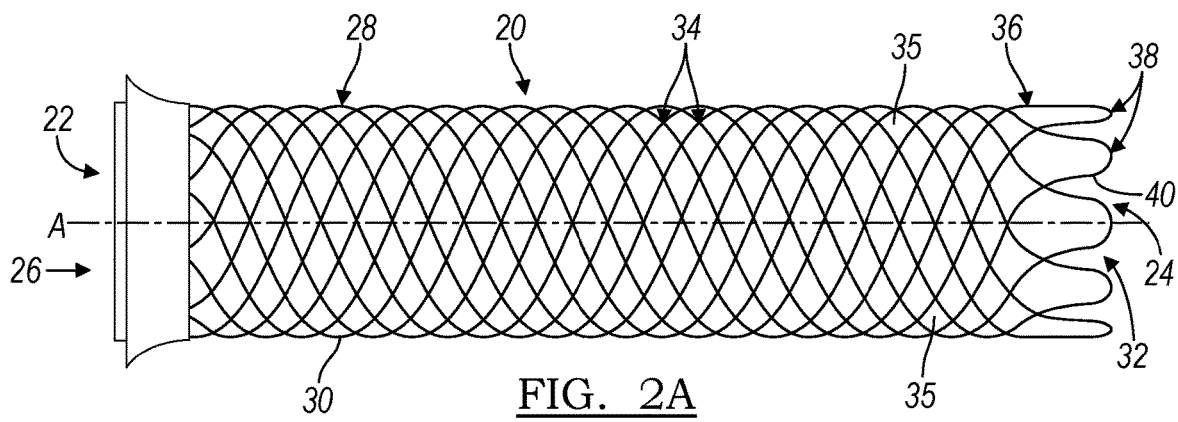
FIG. 2A is a side view of a braided stent constructed in accordance with the principles of the present invention showing certain geometric features of the device.
Figure 2B:
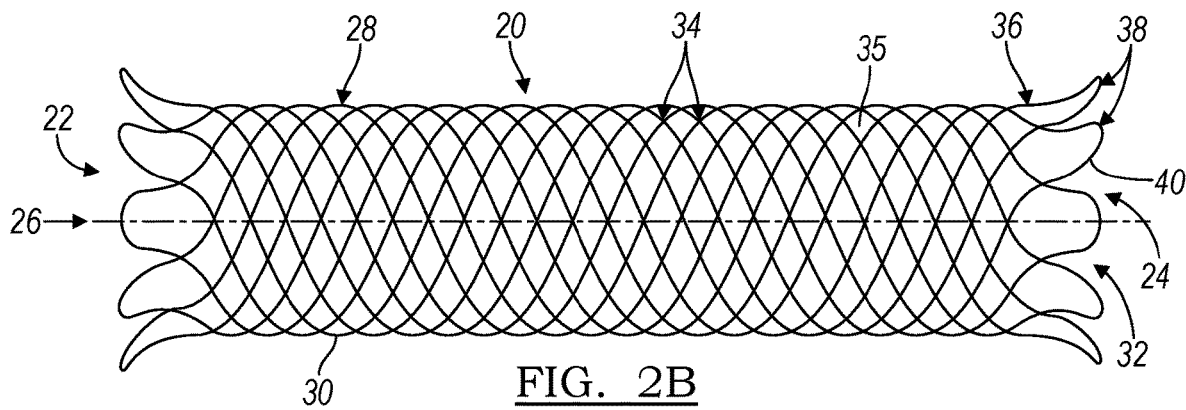
FIG. 2B is a side view of a braided stent constructed in accordance with the principles of the present invention.

In contrast to the stent of FIG. 1, FIG. 2A and FIG. 2B depict a braided stent 20 with features that prevent such fracturing and entangling. The stent 20 extends from a first end 22 and has a tubular body 28 that extends to second end 24. The tubular body 28 may be made, in some embodiments, of a single wire 30 which is braided to take on the desired tubular shape with the appropriate dimensions. The wire 30 crosses itself to create a plurality of braided junctions 34. The tubular body 28 defines a lumen 26 which runs through the device, as well as longitudinal axis A. The lumen 26 extends from first end 22 to second end 24, both ends being open ends. The stent 20 is movable between a compressed (or delivery) configuration, which has a compressed diameter, and an expanded (or deployment) configuration, which has an expanded diameter. The expanded diameter may further refer to the constrained diameter, in which the device is expanded but deployed to a body vessel, and an unconstrained diameter, in which the device is free of any external compression. In general, the middle tubular section will have substantially the same constrained diameter as its unconstrained diameter, or the unconstrained diameter will be somewhat larger than the constrained diameter. For example, a stent with a 5.4 mm unconstrained diameter may be suitable to place in a body lumen which is about 4.0 mm in diameter. In any case, the constrained diameter of any flare will be less than its unconstrained diameter. In some embodiments, the stent may have an oversized diameter in the unconstrained configuration relative to the vessel into which it is to be implanted by about 0.0 mm to about 1.5 mm, or about 0.0 mm to about 1.3 mm, or about 0.0 mm to about 1.1 mm, or about 0.0 mm to about 1.0 mm, or about 0.1 mm to about 1.5 mm, or about 0.1 mm to about 1.3 mm, or about 0.1 mm to about 1.1 mm, or about 0.1 mm to about 1.0 mm, or any value between.

Each of first end 22 and second end 24 include a portion referred to as crown 32. The crown 32 defines an end portion of the device, which includes a plurality of tips 38 which are the most extreme portions of the device in the axial dimension. As depicted in FIGS. 2A and 2B, the tips 38 may be rounded tips having a curved structure.

In some embodiments, crown 32 has a flare 36 (shown in FIG. 2A as an outline to emphasize the flare geometry), which causes the device to curve radially outward and increase in diameter. The flare 36 may be formed at first end 22, at second end 24, or at both ends. The flare 36 may increase the diameter in substantially linear fashion, or its profile may be defined by a curve. The flare 36 provides local stiffness and combats the tendency of the ends of the braided stent 20 to curve radially inwardly, yielding a cigar-like shape. To improve wall apposition, the inward turning of the ends is to be avoided.

FIG. 2A is view of the braided stent 20 with a schematic view of the flare 36, and in which the crown 32 at second end 24 has its flare 36 in a compressed configuration, whereas FIG. 2B is view of stent 20 with both flares 36 unconstrained radially. In the unconstrained configuration, the second diameter of the crown may be about 20% to about 40%, or about 25% to about 35%, or about 30% to about 34%, greater than the first diameter of the central tubular body, or any value in between these endpoints.

End segments 40 in crown 36 are formed with tips 38, and have a three-curved structure, inclusive of first curve 42, second curve 44, and third curve 46. These features can be seen in FIGS. 3A and 5. Second curve 44 lies between first curve 42 and third curve 46. Second curve 44 transitions into first curve 42 and is connected to first curve 42, and second curve 44 transitions into third curve 46 and is connected to third curve 46. First curve 42 has a first radius of curvature, second curve 44 has a second radius of curvature, and third curve 46 has a third radius of curvature. The first radius of curvature and the third radius of curvature each differ from the second radius of curvature. In some embodiments, the first radius of curvature is different from the third radius of curvature. In other embodiments, the first radius of curvature is equal to, or substantially equal to, the third radius of curvature.

The device according to the principles of the present invention is a self-expanding device. Such devices are expandable from a collapsed or compressed configuration to an expanded configuration. Such a device may be made from a biocompatible material, or a material which is able to be made biocompatible. Examples of suitable materials include, without limitation, nickel-titanium alloys, cobalt-chromium alloys, nickel-chromium alloys, nickel-cobalt-chromium alloys, nickel-cobalt-chromium-molybdenum alloys, nickel-titanium-chromium alloys, and other shape memory and/or superelastic materials, including alloys which include at least one of molybdenum, tantalum, titanium, palladium, and platinum. Polymers and composite materials may also provide the properties necessary for making such a device.

A variety of braiding patterns are possible for a braided stent 20. Although a one-under and one-over pattern is illustrated in the Figures herein, it is also possible to employ, for example, two-under and two-over patterns. The filament or wire 30 may be of any suitable cross-sectional shape. For example, the filament or wire 30 may be flat in shape, or may have a circular-shaped cross-section. The filaments or wires may have any suitable diameter, guided by the final dimensions intended for the device. In one embodiment, the wire 30 is made of a shape memory material, in some instances a nickel-titanium alloy. In some embodiments, the wire may include a soft metal, such as an amount of platinum. The wire 30 in some embodiments may be 0.003-inch in diameter and nickel-titanium alloyed with 30% platinum, in order to provide superlasticity, shape memory, and radiopacity.

Figure 3A:
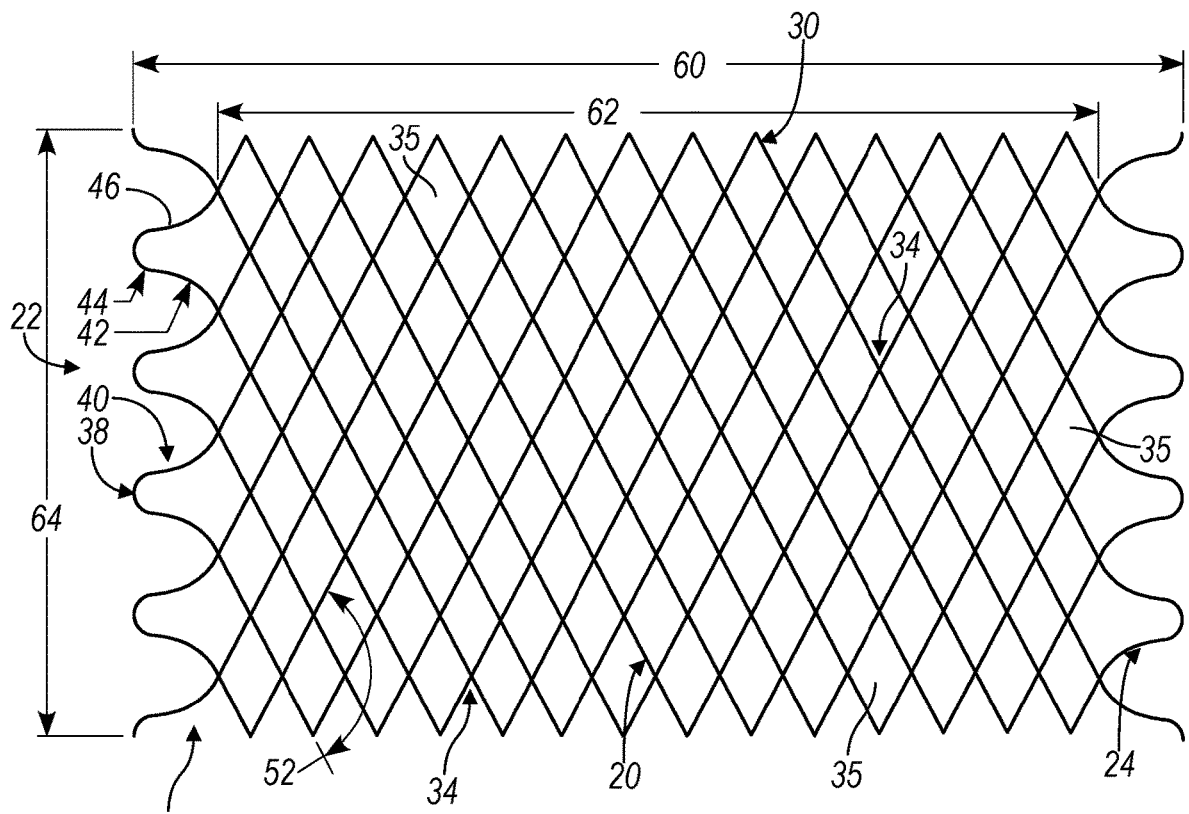
FIG. 3A is a schematic view of a stent constructed in accordance with the principles of the present invention.

FIG. 3A provides a flattened, schematic plan view of a braided stent 20 in accordance with the principles of the present invention. The view of FIG. 3A represents a fully-braided stent which has been cut in a straight line axially at the midpoint of a tip 38 and intersecting a plurality of braided junctions 34 along the length of the cut, with no flare illustrated. The stent 20 has a full length 60 and an internal length 62, the internal length 62 representing the non-flared, substantially cylindrical portion of the device 20. In some embodiments, the internal length 62 may be between about 70% to about 96% the full length 60, or about 80% to about 90% of the full length 60, or about 82.5% to about 87.5% the full length, or about 85%, or any measure in between. Thus, each crown 32 represents about 2% to about 15% the length of the device 20, or about 5% to about 10%, or about to about 6.25% to about 8.75%, or about 7.5% the length of the entire device. The braided wire 30 defines a plurality of pores 35, which are voids between portions of the wire.

In another embodiment, the internal length may be less than 70% of the length of the entire device. In such an embodiment, only the central 70%, or 60%, or 50%, or 40%, or 30%, or 20%, or 10%, or 0%, or any value between 0% and 70% may be a tubular portion of consistent diameter. In the case where the central portion is 0% tubular, this is taken to mean that the device is flared across 100% of its length, and the center of the device represents a local minimum in diameter, the diameter of the device increasing therefrom in both directions so that the entire device may be considered flared.

The device 20 may have a circumference 64 which is between 35% to about 65%, or about 40% to about 60%, or about 45% to about 55%, or about 50% the length 60 of the stent 20. However, in other embodiments the device 20 may extend to a greater length, or be shorter than the aforementioned, as long as the braid angle is maintained along its length.

In the illustrated embodiment, the large angle formed by the wire 30 at the braid junctions 34, known as the strut angle, is about 127 degrees. Half of this measure defines a quantity referred to as the braid angle, which in this case is 63.5 degrees. The braid angle in the unconstrained configuration may be from about 45 degrees to about 85 degrees, or about 50 degrees to about 80 degrees, or about 55 degrees to about 75 degrees, or about 60 degrees to about 70 degrees, or about 62.5 degrees to about 67.5 degrees, or about 62 degrees, or about 65 degrees, or about 68 degrees, or about 70 degrees, or about 72 degrees, or about 75 degrees, or about 78 degrees, or about 80 degrees, or about 82 degrees, or about 85 degrees, or any value between about 45 degrees to about 85 degrees, depending upon the application.

Figure 3B:
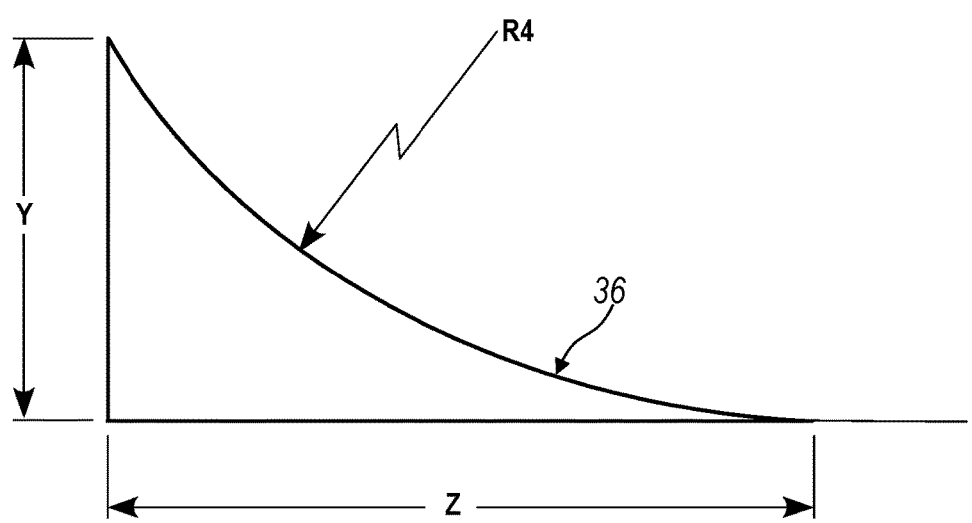
FIG. 3B is a schematic view of measures of a flare profile for the device of FIG. 3A.

In the case where an end 22 or 24 has a flared profile, the dimensions of the flare 36 may contribute to the overall efficacy of the device. As shown in FIG. 3B, the flare 36 may flare a distance of Y outward from the cylindrical body of the device 20, over an axial length represented by Z. The flare 36 curves with a radius of curvature of R4, which in some embodiments may be substantially equal to that of distance Z. The distance Y is about 10% to about 25% of the unconstrained diameter of the stent, or about 12.5% to about 22.5%, or about 12.5% to about 20%, or about 14% to about 18%, or about 15% the unconstrained diameter of the tubular portion of the stent.

The device 20 as depicted in FIGS. 3A and 3B may be a device 20 for fitting to a 2.5 millimeter (mm) to 3.0 mm diameter blood vessel. In one example, the length 60 is about 17.119 mm, and the internal length 62 is about 14.400 mm. The circumference is about 8.731 mm, and the flare 36 extends about 0.459 mm away from the cylindrical portion of the stent 20 when in the expanded configuration. The values of X, Y, Z, and R4 are 0.158 mm, 0.459 mm, 1.000 mm, and 1.001 mm respectively. In the end view of FIG. 4A, the tips 38 of end 24 of the stent can be seen in its deployed configuration 50 when implanted into a 2.5 mm vessel. In FIG. 4B, the tips 38' of second end 24' are shown in the deployed configuration 50' when deployed to a vessel having a diameter of 3.0 mm.

As mentioned, the end segments 40 in the crowns 32 have a three-curved configuration. As shown in FIG. 5, the first curve 42, the second curve 44, and the third curve 46 can be seen. The transition point between the first curve and the second curve is the inflection point at which the wire proceeds from a concave arc to a convex bend, with concave being defined as the point at which a radius of curvature is measured from a center point external to the end segment 40, and convex meaning that the center of the bend is within the space of the end segment 40. The tip 38 is contained within second curve 44. The transition point between the second curve 44 and the third curve 46 is the point at which the wire 30 proceeds from a convex bend to a concave arc.

The radius of curvature R1 of second curve 44 is smaller than the radius of curvature R2 of first curve 42, and than R3 of third curve 46, yielding a sharper bend than the two concave curves. In one embodiment, R2 is about one-quarter to about one-half (about 25% to about 50%) of R1 and of R3, or about 27.5% to about 42.5%, or about 28% to about 35%, or about 29% to about 32.5%, or about 29%, or about 30%, or any value in between. In some embodiments, R1 is substantially equal to R3. In the embodiment of FIG. 3A, R1 and R3 are about 1.138 mm, and R2 is about 0.338 mm.

In another embodiment, the radius of curvature R1 of the first curve 46 may be mathematically determined based on the radius of curvature R2. An equation to determine the measure of R1 or R3 in such an embodiment may be:

$$R1 (\text{or } R3) = \frac{\frac{\pi D}{2(CN)} - R2}{1 - \cos \alpha}$$

In the equation above, D is the unconstrained diameter of the central portion of the stent, CN is the number of tips on an end of the stent, and a is the braid angle of the wire. Thus, the transition radius, in some embodiments, may be related to not only R1, but the stent diameter, the number of tips, and the braid angle.

Because of the construction of the device, including the tri-curved structure 40 at one end or both ends of the device 20, the braided stent 20 can be compressed to a small size in the radial dimension. In one instance, the braided stent 20 can be crimped to fit into a 0.027-inch microcatheter without being damaged, such as permanent setting or fracturing. In other cases, the stent 20 can be crimped to an internal diameter of 0.017 inch, or less than 0.017 inch. This allows for simpler introduction into a vessel of the neurological system due to its small size.

Figure 6A:
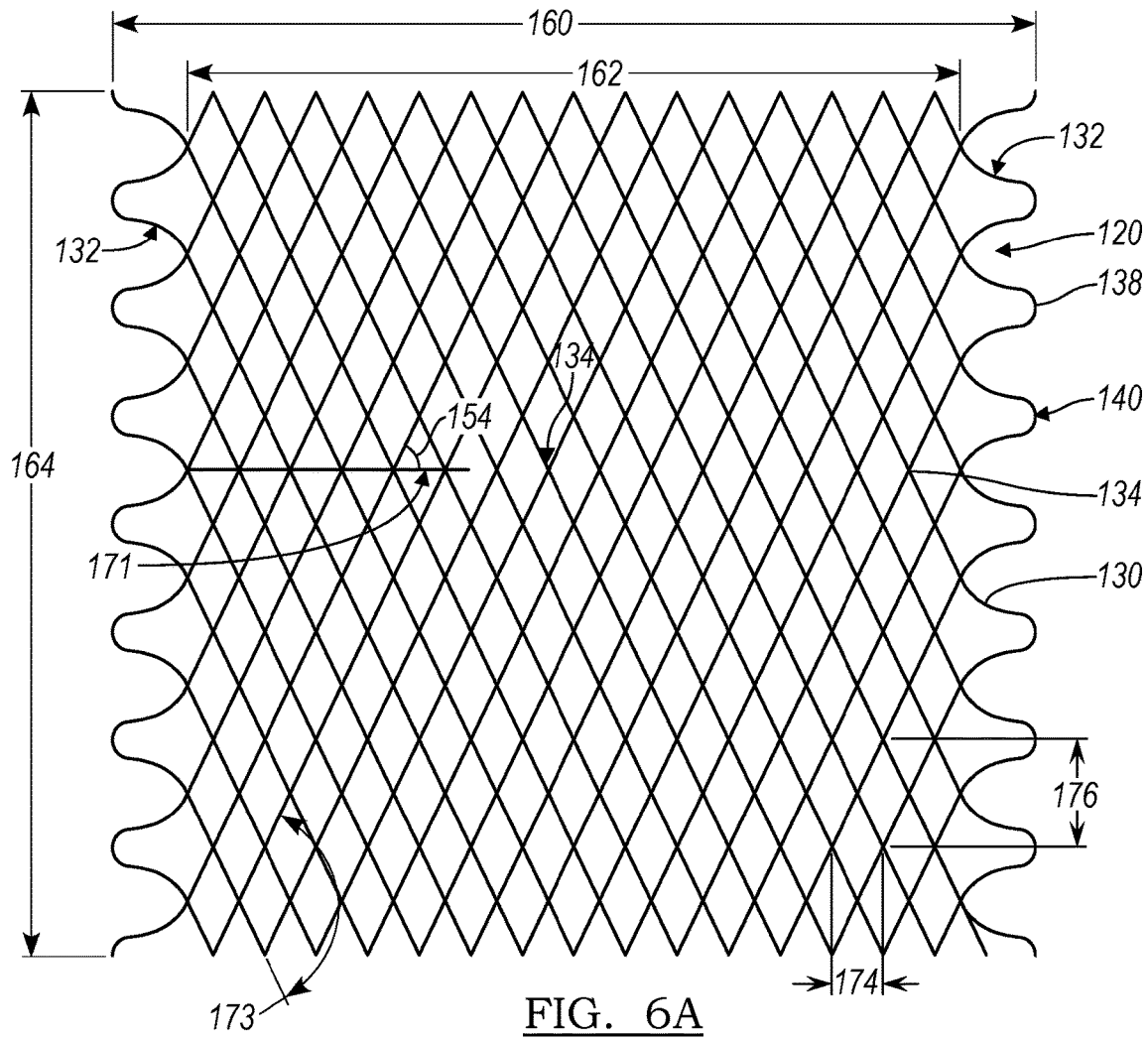
FIG. 6A is a schematic view of a plan for a braided stent displaying geometric features in accordance with another embodiment of the present invention.
Figure 6B:
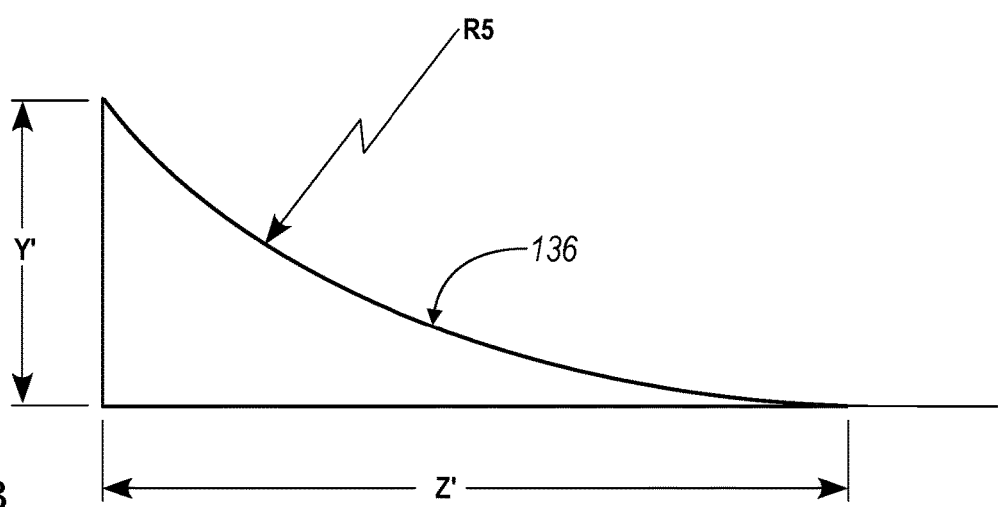
FIG. 6B is a schematic view of a flare profile of the device of FIG. 6A.

FIG. 6A illustrates another device 120 having an overall length 160, an internal length 162, and a circumference 164. The device 120 of FIG. 6A has 8 crowns 132, as opposed to the 5 crowns 32 of the previous figures, but the length 160 is substantially the same as the length 60; thus this device yields a greater diameter than that of FIG. 3A. FIG. 6B illustrates a flare 136.

Figure 7A:
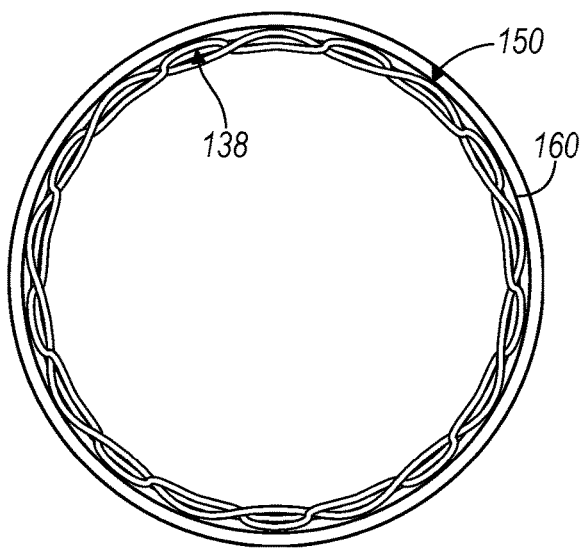
FIG. 7A is an end view of a braided stent constructed in accordance with the principles of the present disclosure, showing wall apposition when implanted into a vessel of a first diameter.
Figure 7B:
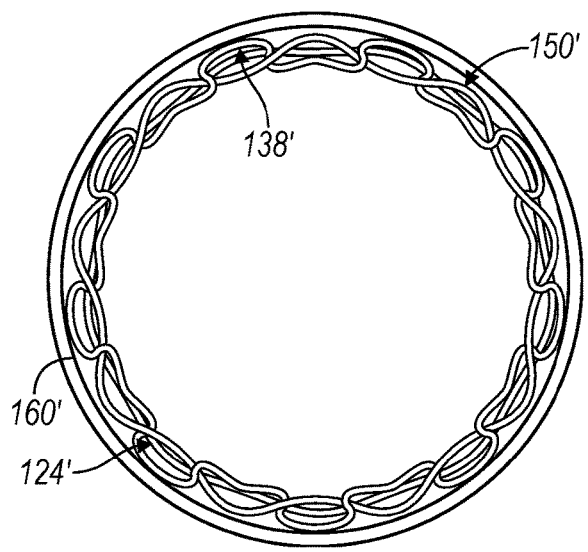
FIG. 7B is an end view of the braided stent of FIG. 7A showing wall apposition when implanted into a vessel of a second diameter.

In one embodiment, the device 120 is about 17.023 mm long, with an internal length 162 of 14.250 mm. The circumference 164 of the device is about 16.015 mm, and the wire 130 forms a braid angle 154 of about 64.5 degrees at braided junction 134, as measured from bisecting line 171, thereby making full angle 173 to have a measure of 129 degrees. R1 of first curve 142 and R3 of third curve 146 of the end segments 140 is about 1.160 mm, and R2 of second curve 144 is about 0.338 mm. The flare 136 extends about 0.738 mm away from the cylindrical body radially, over an axial length of Z' of about 1.815 mm, at a radius of curvature R5 of about 2.578 mm. The stent of such dimensions has an outer diameter of about 5.4 mm. A stent of these dimensions may be indicated for a 4.0 mm-5.0 mm vessel. The apposition of such a stent deployed to a 3.9 mm diameter vessel 160 is shown in expanded configuration 150, as shown in FIG. 7A. The device 120' is shown in a 5.0 mm vessel 160' in expanded configuration 150', illustrated in FIG. 7B.

Figure 6C:
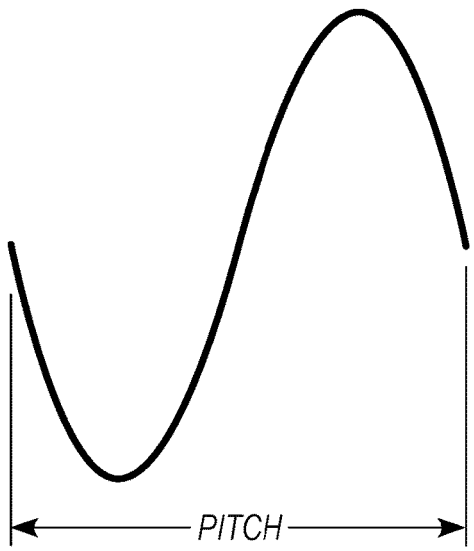
FIG. 6C is a schematic side view representing the helical pitch of a section of braid as described herein.
Figure 6D:
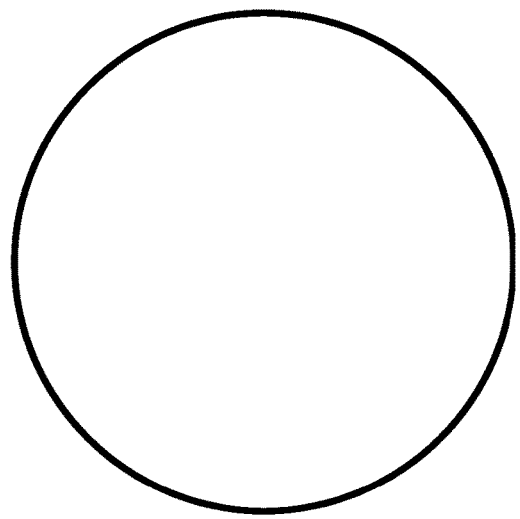
FIG. 6D is a schematic end view representing the helical pitch of a section of braid as described herein.

Parameters of the device that define the sizing of the first, second and third curves of the end segments 40/140 are illustrated in FIGS. 6A, 6C, and 6D. The wire 30/130 is braided in helical stretches across the length of the device. The helices have a pitch, which is defined as the linear length that it takes for the wire 30 to make a single, 360-degree turn about the body of the device. A side view of the pitch is shown in FIG. 6C, and the end view (which is a circle) is shown in FIG. 6D.

In some embodiments, the helical pitch of the wire 30/130 is about two times to about eight times the measure of the first radius of curvature R1/R1', or about 3.5 times to about 7 times, or about 4 times to about 5 times, or any value in between these endpoints.

In some embodiments, the first diameter of the central, tubular region of the device in the expanded, unconstrained configuration is about 1.5 times to about 5 times the first radius of curvature R1/R1', or about 2 times to about 4 times, or about 2.5 times to about 3 times, or any value between these endpoints.

The braid angle 54/154 is defined as the inverse tangent of (pi*D/pitch), wherein D is the diameter of the stent in the central section at when in the unconstrained configuration. Each cell, which in the illustrated embodiment have a diamond shape, has a cell height 176 which has dimensions pi*D/N, where N is the number of crown tips 38/138. The cell width 174 is the cell height 176 divided by the tangent of the braid angle 54/154, which as described previously, is determined by bisecting the angle formed at a braided junction 134 (illustrated by line 171 in FIG. 6A.)

In some embodiments, the helical pitch of the wire 30/130 is about three times to about eight times the first radius of curvature R1/R1'.

In certain embodiments, the apices of the braided stent 20/120 may come into contact with one another as the stent is moved to its compressed or delivery configuration. In some instances, this is acceptable, as the stent will ultimately resolve this head-to-head contact (if it occurs) when compressed further. However, there is a possibility that the apices will endure significant strain due to compression and from the contact during this procedure prior to resolution. Too much strain may cause the material to permanently set, which in turn may prevent the device from functioning properly. Thus, in some instances, it may be beneficial to incorporate an out-of-plane twist of the apices including the tips in order to minimize this contact, or avoid it entirely.

An end view of a stent 300 with twisted apices 381 is a shown in FIG. 8A. The twist is indicated by the twisted arrow. The twist may be about 5 degrees to about 40 degrees, or about 10 degrees to about 30 degrees, or about 15 degrees, or about 20 degrees, or about 25 degrees, or any quantity between about 5 degrees and about 40 degrees, as measured using the description below.

The twist may be in either direction: either following the braiding direction (illustrated by the curved arrow of FIG. 8A), or away from the braiding direction. In some instances, it will be desirable to form the twist in the same direction as the braid in order to avoid unwinding of the braiding.

FIG. 8B illustrates an apex of the device of FIG. 8A. The first curve 342, the second curve 344 including tip 338, and the third curve 346 are illustrated. Reference points 383a and 383b are indicated. These points lie opposite and equidistant from the point defining the tip 338, and are separated by distance 382.

FIG. 8C is a schematic view of the five-apex device 300 of FIG. 8A. The outer edges of the apices define a circle with center 387 and radius 385. Radius 385 passes through the reference point 383a and meets the circle at point 396. Line 397 is tangent the circle. Line 388 passes through reference point 383a and is parallel to tangent line 397.

Line 394 passes through reference points 383a and 383b, and roughly follows the profile of a single apex. Line 394 and radius 385 meet at angle 386, and line 394 and parallel line 388 meet at twist angle 389. The twist angle 389 as shown in FIG. 8C is about 15 degrees. In one embodiment, all apices of an end of the device are twisted by the same twist angle 389.

An angle of about 15 degrees avoids collisions between the apices as they are compressed and come together in the compressed or delivery state. FIG. 9A shows an intermediate phase of the compression, with partially compressed state 390. The tips 338 are brought closer to center 387, but pass by one another due to the twist of about 15 degrees apiece. As shown in fully collapsed state 392 in FIG. 9B, the tips 338 have moved over the adjacent apex in the direction of the braid, and under the adjacent apex in the opposite direction, leading to a collision-free compression.

It will be appreciated that other methods of twisting the apices or tips may be employed in the device constructed in accordance with the principles of the present disclosure as is known in the art.

The braided stent 20/120 in accordance with the principles of the present disclosure may be used for a variety of applications, including coiling procedures for aneurysms. FIG. 10 provides a view of one such method.

In a first step 200, a delivery system as is known in the art can be percutaneously introduced into a site of an aneurysm, including an intracranial aneurysm. In a second step 210, the braided stent 20/120 is placed across a neck portion of the aneurysm, bridging the aneurysm. In a third step 220, the delivery system is operated (such as by pulling a sheath toward the practitioner) to release the self-expanding braided stent 20/120, allowing the stent to expand and be implanted across the aneurysm.

In a fourth step 230, a coil delivery catheter may be fed through the spaces or cells defined by the braid of the braided stent 20/120, and adjusted such that it points into, or is located within, the aneurysm. In a fifth step 240, at least one coil (such as a platinum coil) as is known in the art, is introduced into the aneurysm. In another embodiment, the fifth step 240 may include introducing an embolic material as is known in the art into the aneurysm, in addition to or instead of the at least one coil. In a sixth, optional step 250, the procedure may be monitored by a visualization method, including fluoroscopy and radiography. This step may be employed in parallel with repeating coil deployment step 240 as many times as is necessary to fill the aneurysm. In a seventh step 260, the delivery assembly and catheter are withdrawn from the patient. Other method steps may be included at any other point in the procedure, as is known in the art.

In some embodiments, the method steps may be practiced consecutively, as detailed in the flow of FIG. 10 and as described above. In other embodiments, the order of certain steps may be changed as a practitioner finds suitable. For instance, in some cases the aneurysm may first be filled with at least one coil or a mass of embolic material, and after this the stent which bridges its neck may be implanted.

As a person skilled in the art will readily appreciate, the above description is only meant as an illustration of implementation of the principles this application. This description is not intended to limit the scope of this application in that the system is susceptible to modification, variation and change, without departing from the spirit of this application, as defined in the following claims.

What is claimed is:

1. A stent comprising:
a wire braided into a tubular body comprising a proximal end and extending to a distal end, the tubular body having an expanded configuration and a collapsed configuration and terminating in a crown in at least one of the proximal end and the distal end, the crown defining a plurality of rounded tips, each rounded tip comprising a first bend, a second bend, and a third bend, the second bend being positioned between and connected to the first bend and the third bend, the first bend being concave and having a first radius of curvature, the second bend being convex and having a second radius of curvature between about one-half to about one-quarter the first radius of curvature, and the third bend being concave and having a third radius of curvature between about twice to about four times the second radius of curvature.

2. The stent of claim 1, wherein the tubular body further comprises a central portion having a first diameter, and a flared end portion extending to an end having a second diameter greater than the first diameter.

3. The stent of claim 2, wherein the flared end portion comprises a crown.

4. The stent of claim 1, comprising a crown at each of the proximal end and the distal end of the tubular body.

5. The stent of claim 2, wherein the first diameter in the expanded configuration is between about three times to about twelve times the first diameter in the collapsed configuration.

6. The stent of claim 1, wherein the first radius of curvature is substantially equal to the third radius of curvature.

7. The stent of claim 2, wherein the crown is about 2% to about 15% the length of the stent.

8. The stent of claim 1, wherein a helical pitch of the wire is about two times to about eight times the first radius of curvature.

9. The stent of claim 1, wherein the first diameter in the expanded configuration is about 1.5 times to about 5 times the first radius of curvature.

10. The stent of claim 2, wherein the second diameter is about 20% to about 40% greater than the first diameter.

11. The stent of claim 1, wherein the wire comprises a shape memory material.

12. The stent of claim 1, wherein a diameter in the collapsed configuration is between about 0.43 millimeter and about 0.69 millimeter, and a diameter in the expanded configuration is between about 2.5 millimeters and about 5 millimeters.

13. A stent for treatment of an intracranial aneurysm, the stent comprising:
a wire braided into a tubular body comprising a proximal end and extending to a distal end, the tubular body having an expanded configuration and a collapsed configuration and comprising:
a central portion having a first diameter in the expanded configuration,
a proximal portion extending proximally from the central portion to a proximal end and comprising a proximal crown, the proximal portion being flared such that the proximal end has a larger diameter than the first diameter in the expanded configuration,
a distal portion extending distally from the central portion to a distal end and comprising a distal crown, the distal portion being flared such that the distal end has a larger diameter than the first diameter in the expanded configuration, each of the proximal crown and the distal crown defining a plurality of rounded tips, each rounded tip comprising a first bend, a second bend, and a third bend, the second bend being positioned between and connected to the first bend and the third bend, the first bend and the third bend being concave and having a first radius of curvature, the second bend being convex and having a second radius of curvature between about one-half to about one-quarter the first radius of curvature.

14. The stent of claim 13, wherein the stent terminates at the plurality of rounded tips.

15. The stent of claim 13, wherein the diameter of the proximal end is substantially equal to the diameter of the distal end when in the expanded configuration.

16. The stent of claim 13, wherein the wire comprises a shape memory material.

17. The stent of claim 13, wherein the first diameter in the expanded configuration is between about three times to about twelve times the first diameter in the collapsed configuration.

18. The stent of claim 13, wherein the diameter of the central portion in the collapsed configuration is between about 0.43 millimeter and about 0.69 millimeter, and the first diameter is between about 2.5 millimeters and about 5 millimeters.

19. The stent of claim 1, wherein each rounded tip includes an out-of-plane twist.

20. The stent of claim 19, wherein the twist is in the same direction as a direction of braiding of the braided wire of the tubular body.

* * * * *